United States Patent

Isaka et al.

[11] Patent Number: 5,482,598
[45] Date of Patent: Jan. 9, 1996

[54] MICRO CHANNEL ELEMENT AND METHOD OF MANUFACTURING THE SAME

[75] Inventors: Kazuo Isaka, Tokyo; Takayuki Yagi, Yokohama; Takeshi Miyazaki, Ebina, all of Japan

[73] Assignee: Canon Kabushiki Kaisha, Tokyo, Japan

[21] Appl. No.: 160,857

[22] Filed: Dec. 3, 1993

[30] Foreign Application Priority Data

Dec. 8, 1992 [JP] Japan ................................. 4-328119

[51] Int. Cl.6 ................................. C25F 3/12; C25F 3/30
[52] U.S. Cl. ................................. 204/129.55; 204/129.65; 204/129.75; 204/130; 437/170; 437/247
[58] Field of Search ................................. 204/130, 140, 204/129.55, 129.65, 129.75; 437/170, 247

[56] References Cited

U.S. PATENT DOCUMENTS

| | | | |
|---|---|---|---|
| 3,397,278 | 8/1968 | Pomerantz | 174/52 |
| 3,640,806 | 2/1972 | Watanabe et al. | 204/140 |
| 4,092,445 | 5/1978 | Tsuzuki et al. | 427/85 |
| 5,139,624 | 8/1992 | Searson et al. | 204/129.3 |

*Primary Examiner*—John Niebling
*Assistant Examiner*—Arun S. Phasge
*Attorney, Agent, or Firm*—Fitzpatrick, Cella, Harper & Scinto

[57] ABSTRACT

A micro channel element includes a semiconductor substrate and a channel. The micro channel element is produced as follows. A mask having an opening with a desired pattern is formed on a surface of the semiconductor substrate. The semiconductor substrate on which the mask is formed is dipped in a solution of hydrofluoric acid or a solution mixture of hydrofluoric acid and ethyl alcohol. A cathode is arranged near the surface of the substrate dipped in the solution. An anode is connected to the other surface of the semiconductor substrate. A porosity is imparted to a portion of the surface of the semiconductor substrate which corresponds to the opening of the mask by applying a voltage across the cathode and anode. A high-temperature treatment is performed for the semiconductor substrate removed from the solution to increase the pore size and extend the branches of pores of the porous portion on the surface of the semiconductor substrate, thereby forming the micro channel.

17 Claims, 3 Drawing Sheets

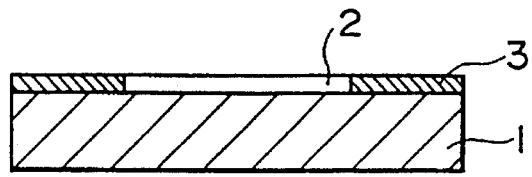
FIG. IA
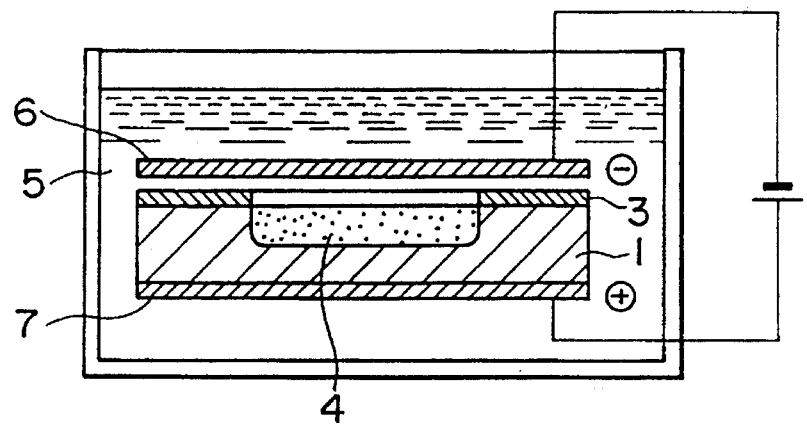
FIG. IB
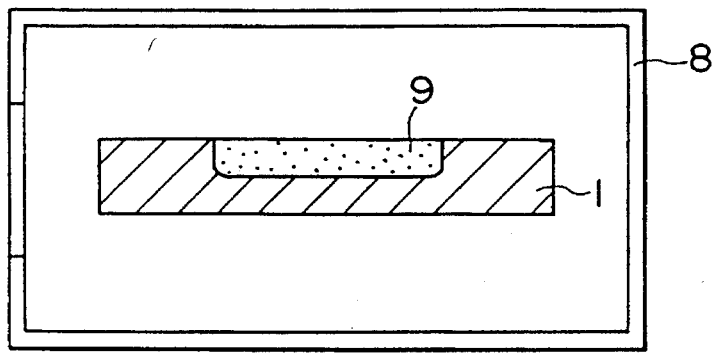
FIG. IC

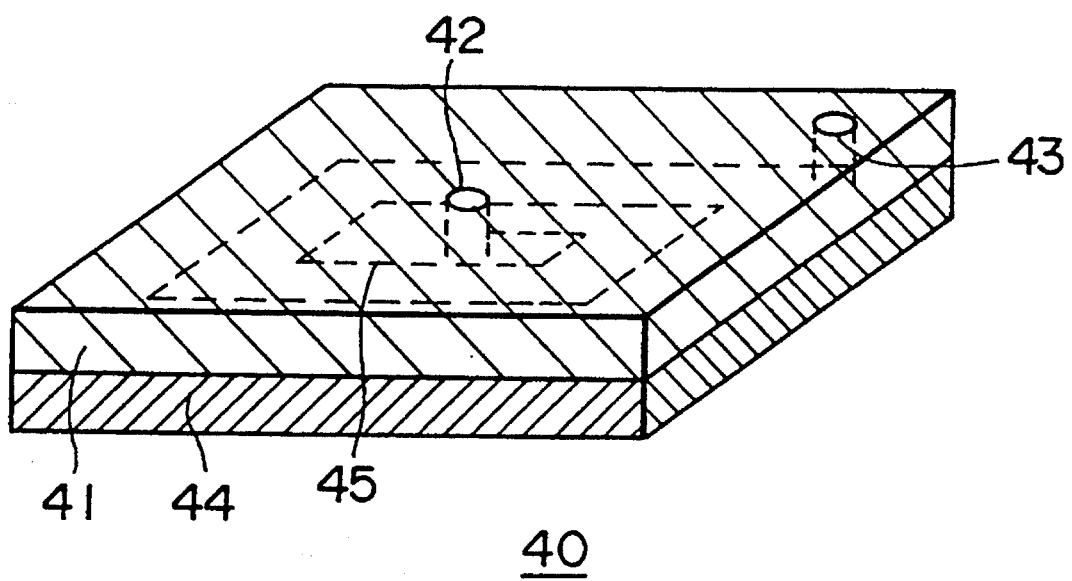
F I G. 3

MICRO CHANNEL ELEMENT AND METHOD OF MANUFACTURING THE SAME

BACKGROUND OF THE INVENTION

1. Field of the Invention

The present invention relates to a micro channel element having a channel capable of passing or separating a fluid, such as a gas or a liquid, and a method of manufacturing the same.

2. Related Background Art

As fluid separating means, a chromatography method has been conventionally used extensively.

For example, a chromatograph apparatus comprising a chromatography element formed on a semiconductor substrate is recently disclosed in "Design of Open-tubular Column Liquid Chromatograph Using Silicon Chip Technology" (Sensors and Actuators, 1990, pp. 249–255). The use of such an element makes miniaturization of apparatuses possible, and this makes it possible to mass-produce apparatuses stable in performance. In a chromatograph apparatus of this type, the separating power of the apparatus is improved by packing porous fine particles in a channel through which a fluid passes, or by performing packing-polymerization of a gel.

In an element formed on a semiconductor substrate, however, a channel for passing a fluid is very narrow; as an example, the diameter of a channel is 10 μm or less in the case of the above-mentioned apparatus. It is very difficult to pack a packing material in such a channel such that the packing material is dispersed evenly and densely.

SUMMARY OF THE INVENTION

It is an object of the present invention to solve the problem of the above conventional technique and provide a micro channel element capable of separating a fluid efficiently without requiring any packing material, and a method capable of easily manufacturing this element.

A micro channel element for achieving the above object of the present invention comprises:

a semiconductor substrate; and a channel formed by imparting porosity to a portion of the surface of the semiconductor substrate.

A method of manufacturing a micro channel element, comprises the steps of:

forming a mask having an opening with a desired pattern on the first surface of a semiconductor substrate;

dipping the semiconductor substrate on which the mask is formed in one of a solution of hydrofluoric acid or a solution mixture of hydrofluoric acid and ethyl alcohol;

arranging a cathode near the first surface of the semiconductor substrate dipped in the solution, and connecting an anode to the second surface of the semiconductor substrate opposite to the first surface;

imparting porosity to a portion of the surface of the semiconductor substrate which corresponds to the opening of the mask by applying a voltage across the cathode and anode; and performing a high-temperature treatment for the semiconductor substrate removed from the solution to increase the pore size and extend the branches of pores of the porous portion on the surface of the semiconductor substrate, thereby forming a micro channel.

BRIEF DESCRIPTION OF THE DRAWINGS

FIGS. 1A to 1C are schematic sectional views for explaining one embodiment of a method of manufacturing a micro channel element according to the present invention;

FIG. 3 is a schematic perspective view showing the second embodiment of the micro channel element according to the present invention.

DETAILED DESCRIPTION OF THE PREFERRED EMBODIMENTS

Figure 2A:
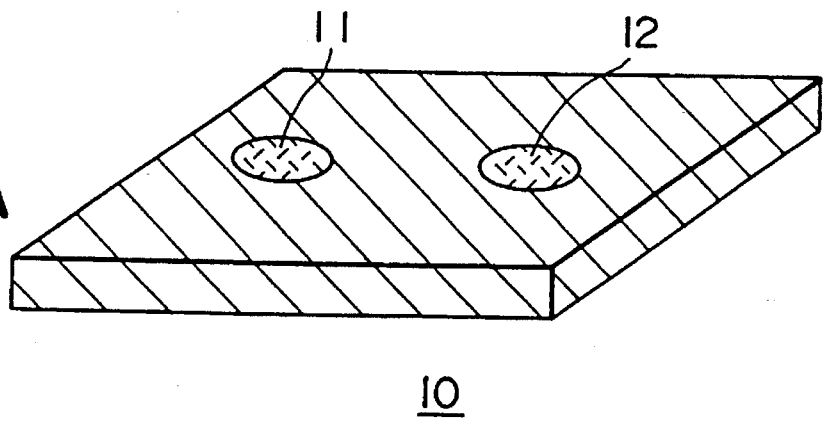
FIGS. 2A to 2C are schematic perspective views for explaining a process of manufacturing the first embodiment of a micro channel element according to the present invention.

The embodiments of the present invention will be described in detail below with reference to the accompanying drawings.

In the present invention, a "fluid" means a gas or a liquid, and the liquid includes one containing fine particles.

In addition, a "micro" channel means a channel with a diameter of several millimeters or less, preferably several hundred μm or less. Although the length of a channel is not limited, it is desirable that the length of a channel be larger than its diameter, preferably 10 μm to 10 m for one element.

FIGS. 1A to 1C are schematic sectional views for explaining an embodiment of a method of manufacturing a micro channel element according to the present invention. First, as shown in FIG. 1A, a mask 3 having an opening 2 with a desired pattern is formed on the first surface of a semiconductor substrate 1. Subsequently, as shown in FIG. 1B, the semiconductor substrate 1 on which the mask 3 is formed is dipped in a hydrofluoric acid solution or solution 5 prepared by mixing ethyl alcohol in hydrofluoric acid. A cathode 6 is arranged near the first surface of the semiconductor substrate 1 dipped in the solution. An anode 7, on the other hand, is connected to the second surface of the semiconductor substrate 1 opposite to its first surface. A voltage is applied across the cathode 6 and the anode 7, thereby imparting porosity to a portion 4 of the surface of the semiconductor substrate which corresponds to the opening of the mask.

In the above porosity imparting process, it is desirable that the concentration of the solution be 5 to 50 vol. %, the temperature of the solution be 5 to 70° C., and the density of a current flowing through the anode upon application of the voltage be 5 to 300 mA/cm².

Subsequently, as shown in FIG. 1C, the semiconductor substrate 1 removed from the solution is placed in a high-temperature oven 8 and treated at a high temperature of 800 to 1,000° C. This high-temperature treatment increases the pore size in the porous portion in the surface layer of the semiconductor substrate, thereby connecting pores in the direction of a channel, and forming a continuous cavity like in a sponge to be referred to as continuous cavity formation hereinafter. In this manner, a micro channel 9 is formed.

The semiconductor substrate need only be one to which porosity can be achieved by anodic formation. The silicon substrate is most preferred since it can be processed by a semiconductor process.

The porous channel may take any given shape such as a linear shape, a curved shape, or a spiral shape, and its porosity is preferably about 10 to 90%.

The micro channel element of the present invention is manufactured by a micro-processing technique, and it is possible to mass-produce the elements by using a series of semiconductor processes. It is also possible to form an IC for controlling conveyance or detection inside the element.

The micro channel element of the present invention can be applied to solid-gas separation and solid-liquid separation as well as separation making use of the difference in flow rate between gases or liquids, and is also applicable to an enzyme reaction by using adsorptivity.

As an application example of the enzyme reaction, an enzyme is immobilized in the porous channel to carry out various reactions; for example, enzyme invertase is immobilized in the porous channel to perform hydrolysis of saccharose, or uricase is immobilized in the porous channel to check the amount of uric acid in serum. Immobilizing an enzyme in a porous channel brings about advantages that, e.g., the reaction solution is not contaminated and the enzyme can be used repeatedly.

In addition, as disclosed in Biochemistry, Vol. 64, No. 2 (1992), page 113, ion column detection in which detection is performed on a capillary having, e.g., a multi-wavelength absorption detector or a fluorescence detector is often performed in electrophoretic chromatography. In this detection, the detection portion of a cell is preferably transparent so that incident light, reflected light, or fluorescence passes through it. In addition, the utilization efficiency of light is increased when the sectional form of the cell is rectangular.

In such a case, manufacturing an element as described below is also a recommendable method. That is, a porous channel 80 μm in depth is formed on the surface of a silicon substrate by using the method mentioned earlier. After this silicon substrate is bonded to a glass, the resultant structure is ground from the silicon side by using a grinder or the like until the thickness of the silicon becomes 20 μm. Thereafter, the resultant silicon surface is bonded to another glass. This makes it possible to manufacture an element both the upper and lower surfaces of which are transparent.

Since an optimal pore size changes in accordance with a substance to be measured, a pore shape appropriate for a given particular substance to be measured can be obtained by selecting a substrate (i.e., selecting the type and concentration of a dopant), adjusting the electrode arrangement and the current during anodic formation, and setting the temperature and the time of the high-temperature treatment.

More detailed embodiments of the present invention will be described below.

First Embodiment

Figure 2B:
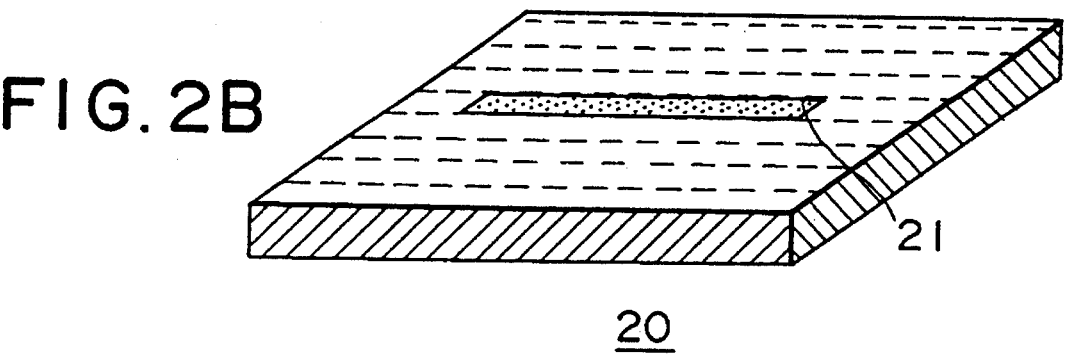
Figure 2C:
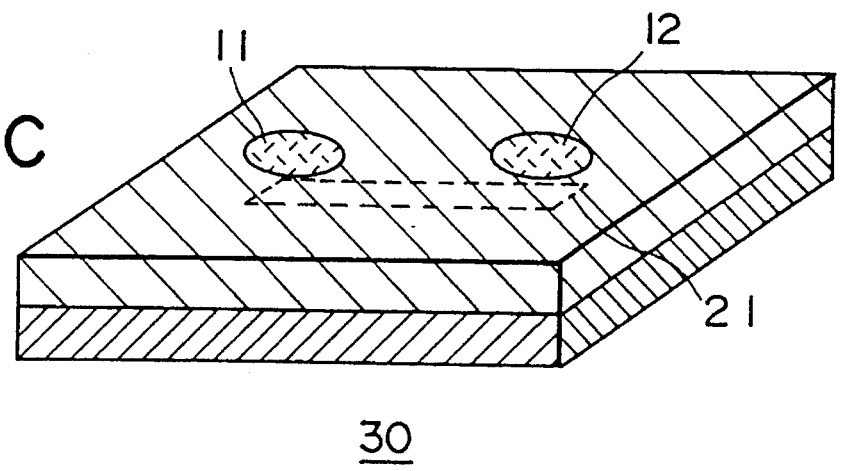

FIGS. 2A to 2C are schematic perspective views showing steps of manufacturing the first embodiment of the micro channel element according to the present invention.

First, pyrex glass was placed in a solution of NaOH, and two electrodes were inserted into the solution. The negative electrode was brought into contact with the pyrex glass while a voltage of 50 V was applied, thereby forming two holes each 0.5 mm in diameter, as an inlet port 11 and an outlet port 12. FIG. 2A illustrates a pyrex glass 10 in which the inlet and output ports 11 and 12 for a fluid were formed.

Masking was performed on a p-type single-crystal silicon substrate 20 with a resistivity of about 0.001 to 100 Ω·cm such that a portion corresponding to a channel to be formed was left behind, and the resultant substrate 20 was dipped in a solution of hydrofluoric acid (HF) with a concentration of 25 vol. %. A platinum electrode was arranged as a cathode near the masked surface of the silicon substrate 20 in the solution, and an anode was connected to the lower surface of the silicon substrate 20. Thereafter, anodic formation was performed at an anode current density of 20 mA/cm² and a solution temperature of 25° C., forming a porous portion in a 3-mm long, 50-μm wide linear non-masked portion on the surface of the silicon substrate to a depth of 30 μm from the surface. Subsequently, a high-temperature treatment was carried out at 850° C. for 60 minutes to increase the pore size of the porous portion, thereby performing continuous cavity formation to obtain a porous channel 21. FIG. 2B illustrates the silicon substrate 20 on the surface of which the porous channel 21 was formed.

Subsequently, the pyrex glass 10 mentioned earlier was overlaid on the surface of the silicon substrate 20 on which the channel was formed such that the inlet and outlet ports corresponded to the channel. The resultant structure was then placed on a heater at 400° C., and a voltage of 200 V was applied to perform anodic bonding. FIG. 2C shows a micro channel element 30 thus manufactured.

A mixture of styrene fine particles and water was injected from the inlet port 11 of the micro channel element 30 manufactured as described above. This mixture was prepared by mixing styrene fine particles 1 μm in diameter into water to have a concentration of 1 nmol.

Of the components of the mixture injected, the water flowed out from the outlet port 12 through the porous channel 21 by capillary action. The styrene fine particles, on the other hand, were left behind in the inlet port 11 since the porous channel 21 functioned as a filter. That is, the water and the fine particles were separated from each other.

Note that removal of unnecessary cells or the like is also possible by the use of the element according to this embodiment.

Second Embodiment

The second embodiment of the present invention in which the micro channel element of the present invention is applied to liquid chromatography will be described below.

FIG. 3 is a schematic view showing an arrangement of a micro channel element 40 according to this embodiment.

A mask on which a pattern of inlet and outlet ports was drawn was placed on a 1.0-mm thick photosensitive glass (trade name: PEG3, available from HOYA CORP.) 41. To facilitate etching, a portion to be etched of the glass was crystallized by being exposed to ultraviolet rays. After re-exposure, etching was so performed as to reach the lower surface of the glass, thereby forming an inlet port 42 and an outlet port 43 each 1 mm in diameter.

A spiral porous channel 45 was formed on the surface of a silicon substrate 44 as follows in correspondence with the inlet and outlet ports 42 and 43. First, a mask consisting of an n-type thin semiconductor layer was formed on the surface of the p-type silicon substrate 44 such that a portion corresponding to the pattern of a channel was left behind. This n-type thin semiconductor layer may be formed by ion injection after formation of an $SiO_2$ layer through thermal oxidation, or may be formed by vapor phase diffusion, an epitaxial process, or the like. Thereafter, the resultant structure was dipped in a 1:1 solution mixture of hydrofluoric acid (HF) and ethyl alcohol at a concentration of 49 vol. %. A platinum electrode as a cathode was placed near the masked surface of the silicon substrate 44 in the solution. The solution was separated into two portions on the upper and lower surface sides of the silicon substrate 44, and the lower surface was connected to an anode via the solution. Anodic formation was then performed at an anode current density of 30 mA/cm² and a solution temperature of 30° C. By using the difference in anodic formation rate between the n- and p-type layers, porosity was given to only the p-type portion. Subsequently, a high-temperature treatment at 1,000° C. was carried out for 40 minutes to increase the pore size and extend the branches of pores of the porous portion, thereby performing continuous bubble formation. As a result, the spiral porous channel 45 was formed.

Subsequently, the photosensitive glass 41 mentioned earlier was overlaid on the surface of the silicon substrate 44 on which the porous channel 45 was formed. While a $CO_2$ laser beam was radiated from the side of the silicon substrate 44, a voltage of 1 kV was applied across the glass and the substrate to perform anodic bonding, thereby completing a micro channel element 40. Since the heating temperature during the bonding can be lowered by carrying out the bonding while radiating light, it is possible to prevent changes in the pore size or the branches of the pores of the porous portion.

A solution mixture of polyethylene glycol (molecular weight: 1,000) and tetraethylene glycol (molecular weight: 242) was flowed into the inlet port 42 of the micro channel element 40 manufactured as described above, and the inlet port was connected to a capillary (not shown) which was coupled to a pump (not shown). The solution mixture was supplied into the porous channel 45 by applying a pressure on the inlet port 42 by using the pump. The solution mixture reached the outlet port 43 while being subjected to separation by the porous channel 45 in passing through the porous channel. The outlet port 43 was connected to a capillary (not shown), and so the solution that had reached the outlet port 43 passed through the capillary and was identified by a differential refractometer.

As a result of the differential refractometry, it was possible to obtain two clear output signal peaks based on the difference in elution time between polyethylene glycol and tetraethylene glycol.

In this embodiment, reversed phase chromatography was performed by using hydrophobic porous silicon. However, it is also possible to use a hydrophilic porous channel by performing thermal oxidation for the porous channel.

In the above two embodiments, the channel was formed in the silicon substrate, and the glass was bonded to manufacture the micro channel element through anodic bonding. The bonding method, however, is not limited to anodic bonding but may be one making use of a general adhesive. It is also possible to form a cover consisting of a film of single-crystal silicon on a silicon substrate on which a channel is formed, since film formation of single-crystal silicon on porous silicon is possible. This makes anodic bonding unnecessary and hence makes it possible to manufacture a micro channel element by using only one silicon substrate.

In addition, the above two embodiments have been described by taking solid-liquid separation and liquid-liquid separation as examples. The elements with the above arrangements, however, can also be used in separation of gases, such as gas chromatography, as well as the applications described in the embodiments.

Furthermore, it is also possible to use the porous channel according to the present invention in combination with a conventional micro channel.

According to the present invention, there can be provided a micro channel element capable of obtaining a sufficient separating power without requiring any packing material.

In addition, since a series of semiconductor processes can be used, it is possible to highly precisely mass-produce fine elements capable of passing and separating a fluid.

What is claimed is:

1. A micro channel element comprising:

a semiconductor substrate; and a channel formed by imparting porosity to only a portion of said semiconductor substrate in a thickness direction from a surface of said semiconductor substrate so as to allow fluid to flow through said channel in a direction along the surface of said semiconductor substrate.

2. An element according to claim 1, wherein said semiconductor substrate comprises of silicon.

3. An element according to claim 1, further comprising another substrate bonded to the surface of said semiconductor substrate and having an opening to allow the fluid to flow into or out from said channel.

4. An element according to claim 3, wherein said another substrate comprises a glass plate.

5. An element according to claim 1, wherein the diameter of said channel is not more than ten millimeters.

6. An element according to claim 5, wherein the diameter of said channel is not more than 100 µm.

7. An element according to claim 1, wherein the length of said channel is 10 µm to 10 m.

8. An element according to claim 1, wherein the porosity of said channel is 10 to 90%.

9. A method of manufacturing a micro channel element, comprising the steps of:

forming a mask having an opening with a desired pattern on a first surface of a semiconductor substrate;

dipping the semiconductor substrate on which the mask is formed into one of a solution of hydrofluoric acid and a solution mixture of hydrofluoric acid and ethyl alcohol;

arranging a cathode near the first surface of the semiconductor substrate dipped into the solution, and connecting an anode to a second surface of the semiconductor substrate opposite to the first surface;

applying a voltage across the cathode and the anode to impart porosity to only a portion of the semiconductor substrate in a thickness direction thereof from the first surface thereof, which corresponds to the opening of the mask; and heating the semiconductor substrate taken out from the solution to a temperature in a range from 800° C. to 1000° C. to increase the pore size and to extend branches of pores of the porous portion on the semiconductor substrate so as to form a micro channel through which fluid can flow in a direction along the first surface of the semiconductor substrate.

10. A method according to claim 9, wherein the semiconductor substrate comprises of a member selected from the group consisting of silicon, aluminum, and iridium.

11. A method according to claim 9, further comprising the step of bonding another substrate having an opening to allow fluid to flow into or out from the channel to the first surface of said semiconductor substrate through anodic bonding.

12. A method according to claim 11, wherein the another substrate comprises a glass plate.

13. A method according to claim 9, wherein the concentration of the solution is 5 to 50 vol. %, the temperature of the solution is 5 to 70° C. and the density of a current flowing through the anode upon application of the voltage is 5 to 300 mA/cm$^2$.

14. A method according to claim 9, wherein the diameter of the channel is not more than ten millimeters.

15. A method according to claim 14, wherein the diameter of the channel is not more than 100 µm.

16. A method according to claim 9, wherein the length of the channel is 10 µm to 10 m.

17. A method according to claim 9, wherein the porosity of the channel is 10 to 90%.

* * * * *

UNITED STATES PATENT AND TRADEMARK OFFICE
CERTIFICATE OF CORRECTION

PATENT NO. : 5,482,598
DATED : January 9, 1996
INVENTOR(S) : Isaka et al.

It is certified that error appears in the above-indentified patent and that said Letters Patent is hereby corrected as shown below:

COLUMN 6:

Line 6, "of" should be deleted.

Signed and Sealed this

Eighteenth Day of June, 1996

Attest:

BRUCE LEHMAN

Attesting Officer        Commissioner of Patents and Trademarks